United States Patent [19]
Lindenbaum

[11] Patent Number: 5,461,030
[45] Date of Patent: Oct. 24, 1995

[54] COMPOSITIONS AND METHODS FOR ENHANCING WOUND HEALING

[75] Inventor: Ella Lindenbaum, Haifa, Israel

[73] Assignee: Life Medical Science, Inc., Princeton, N.J.

[21] Appl. No.: 158,808

[22] Filed: Nov. 29, 1993

[30] Foreign Application Priority Data

Feb. 1, 1991 [IL] Israel .......................................... 097127

[51] Int. Cl.⁶ .......................... A61K 31/74; A61K 38/00; C12N 5/00; C12N 5/02
[52] U.S. Cl. ..................................... 544/4; 514/3; 514/12
[58] Field of Search ........................................ 514/3, 4, 12

[56] References Cited

U.S. PATENT DOCUMENTS

| | | | |
|---|---|---|---|
| 3,664,925 | 5/1972 | Sonenberg et al. | 435/68.1 |
| 3,904,753 | 9/1975 | Sonenberg et al. | 514/12 |
| 4,444,760 | 4/1984 | Thomas, Jr. | 514/12 |
| 4,503,037 | 3/1985 | Szijjarto et al. | 424/94 |
| 4,658,021 | 4/1987 | Goeddel et al. | 530/399 |
| 4,673,649 | 6/1987 | Boyce et al. | 435/240.2 |
| 4,696,917 | 9/1987 | Lindstrom et al. | |
| 4,863,899 | 9/1989 | Todaro . | |
| 4,886,786 | 12/1989 | Lindstrom et al. | |
| 4,940,666 | 7/1990 | Boyce et al. | 435/240.2 |
| 5,013,714 | 5/1991 | Lindstrom et al. | |
| 5,034,375 | 7/1991 | Antoniades et al. | |
| 5,035,887 | 7/1991 | Antoniades et al. | |
| 5,051,443 | 9/1991 | Neufeld et al. | |
| 5,056,520 | 11/1977 | Sonenberg et al. | 530/324 |
| 5,165,938 | 11/1992 | Knighton | 514/2 |
| 5,204,325 | 4/1993 | Lindstrom et al. | |
| 5,218,093 | 6/1993 | Guo et al. | |
| 5,219,739 | 6/1993 | Tischer et al. | |

FOREIGN PATENT DOCUMENTS

| | | |
|---|---|---|
| 308238 | 3/1989 | European Pat. Off. . |
| 0364266 | 10/1989 | European Pat. Off. . |
| 0516901 | 6/1991 | European Pat. Off. . |
| WO9003810 | 4/1990 | WIPO . |

OTHER PUBLICATIONS

Lynch et al *Proc. Nat'l Acad Science USA* 84 1987 pp. 7696–7700.

Diane Krasner, ed. *Chronic Wound Care: A Clinical Source Book for Health Care Professionals* pp. 311–317.

Hayward et al., "Animal Models of Wound Contraction", Clinical and Experimental Approaches to Dermal . . . ,301–312, 1991, Wiley–Liss, Inc.

Mulder, "If Wounds Could Talk", Clinical and Experimental Approaches to Dermal and Epidermal Repair: Normal and Chronic Wounds, 55–66, 1991, Wiley–Liss, Inc.

Liss, Culture of Animal Cells, 238–241, 1988, Alan R. Liss, Inc. New York.

Barnes, et al., "Serum–Free Cell Culture: A Unifying Approach", Cell, vol. 22, 649, 1980.

Ham, "Growth of Normal Human Cells in Defined Media", 16–30.

Tsao et al., "Clonal Growth of Normal Human Epidermal Keratinocytes in a Defined Medium", Journal of Cellular Physiology, 110, 219, 1982.

Wille et al., "Integrated Control of Growth and Differentiation of Normal Human . . . " Journal of Cellular Physiology, 121, 31, 1984.

Boyce et al., "Calcium–Regulated Differentiation of Normal Human Epidermal Keratinocytes . . . " Journal of Investigative Dermatology, 81, 335, 1983.

Pierce et al. "Platelet–derived Growth Factor and Transforming Growth Factor–β Enhance Tissue Repair Activities by Unique Mechanisms", *J. Cell Bio.*, Jul. '89.

Lynch et al. "Role of platelet–derived growth factor in wound healing: Synergistic effects with other growth factors," *Proc. Natl. Acad. Sci. USA*, vol. 84, pp. 7696–7700, Nov. '87.

*Primary Examiner*—Howard E. Schain
*Assistant Examiner*—Lynn Touzeau
*Attorney, Agent, or Firm*—Henry D. Coleman; R. Neil Sudol

[57] ABSTRACT

The present invention relates to formulations and methods for treating wounds utilizing these formulations. The formulations according to the present invention are useful for treating wounds by accelerating wound healing. These formulations comprise an effective amount of a serum free cellular nutrient medium in combination with an effective amount of at least one cellular growth stimulating compound, e.g. a natural anabolic hormone or transforming growth factor.

22 Claims, 2 Drawing Sheets size: 7x3.5x2 cm size: 5.5x2.5x1 cm size: 5x2.5x0.5 cm size: 4.5x2x0.5 cm size: 2.5x1x0 cm

COMPOSITIONS AND METHODS FOR ENHANCING WOUND HEALING

FIELD OF THE INVENTION

The present invention relates to new compositions and methods using such compositions for promoting wound healing of skin. More particularly, the invention relates to wound healing compositions which are based on a serum-free medium specialized to grow epidermal cells in culture in combination with at least one anabolic protein growth hormone or growth factor.

BACKGROUND OF THE INVENTION

A skin wound is defined as a breach in the continuity of any body tissue caused by a minimal direct injury to the skin. There are many instances where a quick closure of the wounded skin will promote a beneficial response. Generally, quick closure of wounded skin can be achieved either by conservative methods such as the application of medicaments, or alternatively, by using various surgical procedures including suturing, split skin grafting or grafting of new skin grown in culture.

The closure of a wound with skin cells is performed using two methods: either by grafting skin grown in culture or alternatively, by split skin grafting. These two methods are applicable, however, only after a suitable base of granulation tissue has first developed in the wound, the development of which may be quite prolonged or complicated. Split skin grafting, although more common, requires compositions which contain materials for maintaining organ viability and treatment of the wounds for the repair of injury to the skin.

Among the most common injuries to skin include burns. Burn causes destruction of the epidermis and deeper cutaneous and subcutaneous tissues, most of which can be regenerated by the normal healing response if the area burned is not extensive or contaminated. Burns cause more than 2,000,000 injuries annually in the U.S.A., and more than 10,000 deaths each year result from serious burn injuries.

S. T. Boyce et al., in *The Journal of Investigative Dermatology*, 81: 33S–40S, 1983) describes compositions based upon a serum-free culture system to culture normal human epidermal keratinocytes. These compositions comprise optimized nutrient medium MCDB 153 supplemented with epidermal growth factor, insulin, hydrocortisone, ethanolamine, phospho-ethanolamine and whole Bovine Pituitary Extract (wBPE). It is mentioned that the wBPE initiates the primary culture and that cellular senescence occurs after about forty population doublings. It has also been reported in the *Journal of Cellular Physiology*, 110, 219, (1982), that the incorporation of Fetal Bovine Serum Protein (FBSP) may replace whole serum for culturing human epidermal keratinocytes and that the presence of F 12 would eliminate the need for wBPE. As presently known, wBPE is not a common reagent which can be easily reproducibly prepared, its constitution not being constant.

J. J. Wille, Jr. et al., in the *Journal of Cellular Physiology*, 121, 31, (1984) describes the effects of growth factors, hormones and calcium on the growth and differentiation of secondary cultures of normal human prokeratinocytes. Clonal growth was achieved when MCBD 153 was supplemented with epidermal growth factor or wBPE, provided that insulin was present. In the absence of insulin both EGF and wBPE are required. It is mentioned that optimal clonal growth occurred in medium containing 10 ng/ml of epidermal growth factor and 0.3 mM calcium.

According to U.S. Pat. No. 4,673,649, compositions are suggested for clonal growth of a population of human keratinocyte cells in a primary culture for the repair of injury to skin, having a characteristic colony-forming efficiency of about 20%. The composition comprises: MCDB 153, epidermal growth factor a concentration range of 1.0 ng/ml to 25 ng/ml and insulin at a concentration range of 0.5 ug/ml to 50 ug/ml. Optionally, the compositions may contain wBPE (whole bovine pituitary extract) at a concentration range of 7 ug/ml to 700 ug/ml, ethanolamine, hydrocortisone, phosphoethanolamine and calcium chloride. In particular, the compositions are useful for growing skin cells for grafting. No mention is made to the possible use of the disclosed compositions to treat wound conditions in vivo, nor to prolong and preserve the viability of stored split skin grafts. In a very recent U.S. Pat. No. 4,940,666 (by the same inventors and as a c.i.p. of the previous U.S. Patent), the same compositions are claimed to be useful for growing a population of human epidermal cells. The purpose of the compositions suggested is for the propogation of skin cells and achieving monolayers, or stratified layers, of keratinocytes to be used for areas on the body without skin. In other words, these compositions are used for the development of cultured skin cells which may be used for grafting. In addition to the above references, other prior art references suggest that epidermal growth factor may enhance wound healing by increasing fibroblast proliferation.

OBJECTS OF THE PRESENT INVENTION

It is an object of the present invention to provide novel compositions useful for accelerating wound healing.

It is another object of the present invention to provide novel compositions which accelerate wound healing and which also prolong the viability of the skin as an organ.

It is yet another object of the present invention to provide novel compositions useful for accelerating wound healing which comprise defined and readily recognized constituents.

It is still a further object of the present invention to provide wound healing compositions which accelerate wound healing by maintaining moisture at the wound surface.

BRIEF DESCRIPTION OF THE INVENTION

The present invention relates to formulations and methods for treating wounds utilizing these formulations. The formulations according to the present invention are useful for treating wounds by accelerating wound healing. These formulations comprise an effective amount of a serum free cellular nutrient medium in combination with an effective amount of at least one cellular growth stimulating compound, e.g. a natural anabolic hormone or transforming growth factor.

In preferred embodiments according to the present invention, the formulations include growth hormone and most preferably human growth hormone as the cellular growth stimulating compound. In general, the cellular growth stimulating compound is included in an effective amount of at least about 0.05 ng/ml of the formulation, with a preferred range of about 0.5 ng/ml to about 50 ng/ml. The amount and type of cellular growth stimulating compound may vary, but the preferred compound is human growth hormone. The preferred amount of human growth hormone to be used will generally depend on the type and size of the wound, but generally and in most of the cases the amount of growth hormone used will be in the range of between about 0.5 ng/ml to about 50 ng/ml.

DETAILED DESCRIPTION OF THE INVENTION

Figure 1A:
Figure 1B:
Figure 1C:
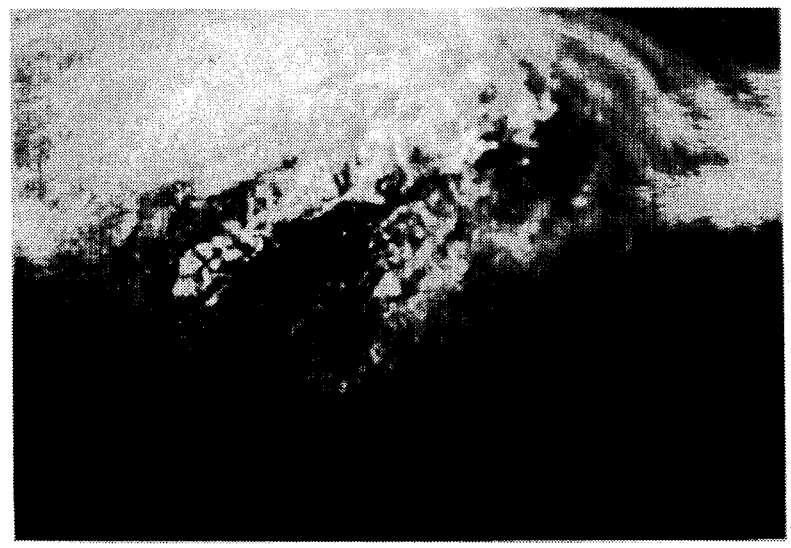

In describing the present invention in the specification, a number of terms will be used.

The term "wound" is used throughout the specification to describe skin wounds which are treated by the formulations and the method according to the present invention. A skin wound is defined herein as a breach in the continuity of skin tissue which is caused by direct injury to the skin. Skin wounds are generally characterized by several classes: punctures, incisions, excisions, lacerations, abrasions and burns. The formulations according to the present invention are useful in varying degrees for enhancing the healing of all wounds of the skin.

The term "delivery polymer" is used throughout the specification to describe a polymer which can be used in combination with a serum free cellular nutrient medium and a cell growth stimulating compound to produce formulations which are preferably used for topical administration to treat wounds according to the present invention. These delivery polymers include, for example, hydrogels, such as hydroxyethylmethacrylate (HEMA), glycerolmethacrylate (GMA) and polyvinylpyrrolidone (PVP), polyethylene glycol (PEG), collagen and gelatin.

The term "serum free cellular nutrient medium" is used throughout the specification to describe a medium which contains no serum, and in combination with a cell growth stimulating compound comprises wound healing compositions according to the present invention. The nutrient medium according to the present invention comprises the following elements: (a) essential amino acids; (b) non-essential amino acids; and (c) vitamins selected from the group consisting of biotin, folate, lipoate, niacinamide, pantothenate, pyridoxine, riboflavin, thiamin and vitamin $B_{12}$. All of these elements (a), (b) and (c) are included in the cell growth stimulating compounds in concentrations and/or amounts effective for enhancing the growth of cells which surround, have been injured by or are responsible for healing a wound. The preferred concentration of essential and non-essential amino acids used in the present invention ranges from about 5.0 um ($10^{-6}$ mole) to about 50 mmol. ($10^{-3}$ mole) The preferred concentrations of vitamins used in the present invention ranges from about 1 nanomole ($10^{-9}$ mol.) to about 10 um. In addition to the elements (a), (b) and (c), the nutrient medium according to the present invention optionally contains any one or more of the following elements: (d) purines and pyrimidines; (e) other organic compounds; (f) major inorganic ions; (g) trace elements; (h) buffers and indicators and (i) other supplements. All of the elements (d), (e), (f), (g), (h) and (i), where they are included in the nutrient medium according to the present invention, are included in amounts effective for enhancing the growth of cells involved in the wound-healing processes. In general, components (d), (e), (h) and (i) range in concentration from about 1 nmol. to about 10 mmol. In the case of components (f) and (h), the concentration ranges from about about 1 umol. to about 50 mmol.

The serum free cellular nutrient medium according to the present invention may include commercially available media. The serum free cellular nutrient medium used may be in the form of a lyophilate which is reconstituted with water, preferably sterilized, distilled water and then supplemented with a cell growth stimulating compound or other additives. Many of the commercially available serum free media are available from commercial suppliers such as Collaborative Research Incorporated, Bedford, Mass. or Biological Industries, Beth HaEmek, Israel. These media may be used as purchased or modified within the scope and practice of the present invention.

The term "cell growth stimulating compound" is used throughout the specification to describe those compounds which are added to the formulations according to the present invention for their known benefits in stimulating the growth and elaboration of cells. Cell growth stimulating compounds for use in the present invention include anabolic protein growth hormones, such as human growth human (GH) and related animal growth hormones, other non-steroidal anabolic hormones, for example, thyroxin ($T_4$), tri-iodothyronine ($T_3$) and insulin, among others, and growth factors, including for example, epithelial growth factor (EGF), fibroblast growth factor (FGF), transforming growth factor (TGF) and insulin-like growth factor (IGF). In the formulations according to the present invention, one or more cell growth stimulating compound is included in an amount effective for stimulating the growth of cells which surround, have been injured by or are responsible for healing a wound. Cell growth stimulating compounds for use in the present invention may include naturally isolated or synthetically produced versions of the above-mentioned compounds or their equivalents and include, where relevant, compounds produced by genetic engineering processes and techniques.

The amount of each component which is used in the formulations according to the present invention will depend upon the type and size of the wound, but each component is included in an amount effective for significantly enhancing the healing of a wound relative to traditional wound healing therapies. In general, in preferred embodiments according to the present invention, the formulations include a cell growth stimulating compound at a concentration of at least about 0.05 ng/ml, preferably about 0.5 ng/ml to about 50 ng/ml. Preferably, the cell growth stimulating compound is human growth hormone, because of its known benefits in promoting the growth and elaboration of cells and its general absence of toxicity.

The preferred human growth hormone is a well-known defined protein which is readily available and results from a pituitary secretion into the blood system. It is constituted from a number of amino acids with a total molecular weight of about 193,000. The human growth hormone which may be used in the present invention can be obtained from a variety of sources, including genetic engineering processes and techniques.

The serum free cellular nutrient medium which is used in the present invention is any nutrient medium having the effect of enhancing recovery of wounded skin tissue when used in combination with the cell growth stimulating compound. In preferred embodiments according to the present invention, the cell growth stimulating compound in an effective amount is mixed into serum free cellular nutrient medium to form the compositions according to the present invention.

The serum free cellular nutrient medium comprises the following groups of constituents: (a) essential amino acids; (b) non-essential amino acids; (c) vitamins; (d) purines and pyrimidines; (e) other organic compounds; (f) major inorganic ions; (g) trace elements; (h) buffers and indicators and (k) other supplements. The groups (d), (e), (f), (g), (h) and (i) are optional. The preferred serum free cellular nutrient medium is modified MCDB.

While not being limited by way of theory, it is believed that the mechanism of the accelerated wound healing, but a plausible explanation could be that the presence of the cellular growth stimulating hormone, and in particular, human growth hormone in the formulations according to the present invention, aims to promote the growth in situ of the granulation tissue, i.e., within the wound itself. At the same time, the novel formulations may also induce the stimulation of the vascular elements and induce growth of vascularized granulation tissue preparatory to split skin grafting. The proliferation of vascularized granulation promotes epidermal growth from the peripheral edges of the wound over the vascular substratum leading to an early closure of the skin over the wound. The mechanism which might be assumed is that during the proliferation phase, new capillaries and fibroblasts appear in the wound from the first day on and reach their maximum levels after one week. The new vessels in granulation tissue originate as budlike structures on nearby vessels, penetrate the wound, become canalized and ramify throughout the wound by cellular division.

It is further believed that the function of the nutrient medium is to provide nutrients to normal, distressed and injured cells which surround or comprise the wound to be treated in order to enhance the growth and repair mechanisms which are responsible for the healing of the wound. In this way, the nutrient medium functions to enhance the ability of the cellular growth stimulating hormone to prmote the elaboration, growth and healing of the wound.

A number of serum free cellular nutrient media may be used in the present invention, including commercially available media or other media well known in the art. Examples of such media (all without serum or having had the serum removed) include ADC-1, LPM (Bovine Serum Albumin-free), F10 (HAM), F12 (HAM), DCCM1, DCCM2, RPMI 1640, BGJ Medium (Fitton-Jackson Modification), Basal Medium Eagle (BME-with the addition of Earle's salt base), Dulbecco's Modified Eagle Medium (DMEM-without serum), Glasgow Modification Eagle Medium (GMEM), Leibovitz L-15 Medium, McCoy's 5A Medium, Medium M199 (M199E- with Earle's salt base), Medium M199 (M199H- with Hank's salt base), Minimum Essential Medium Eagle (MEM-E- with Earle's salt base), Minimum Essential Medium Eagle (MEM-H- with Hank's salt base) and Minimum Essential medium Eagle (MEM-NAA- with non-essential amino acids), among numerous others. These and other useful serum free cellular nutrient media are available from Biological Industries, Bet HaEmek, Israel.

While a large number of serum free cellular nutrient media may be used in the present invention, a preferred nutrient media for use in the present invention is modified MCDB 153.

Experiments which were carried out to prolong the viability of human split graft specimens show that the use of the modified MCDB 153 medium according to the present invention, extended the limit of viability from 3 to 9 weeks. Histological examination of the split skin specimens indicated a strong attachment of the epidermal layer to the dermal substratum in all specimens kept in the modified MCDB 153 medium at 20° C.

Hereafter are enumerated the particular constituents and concentrations of the above groups for MCDB 153:

| | Concentration |
|---|---|
| Group (a): | |
| Arginine | $1.0 \times 10^{-3}$ |
| Cysteine | $2.4 \times 10^{-4}$ |
| Glutamine | $6.0 \times 10^{-3}$ |
| Histidine | $8.0 \times 10^{-5}$ |
| Isoleucine | $1.5 \times 10^{-5}$ |
| Leucine | $5.0 \times 10^{-4}$ |
| Lysine | $1.0 \times 10^{-4}$ |
| Methionine | $3.0 \times 10^{-5}$ |
| Phenylalanine | $3.0 \times 10^{-5}$ |
| Threonine | $1.0 \times 10^{-4}$ |
| Tryptophan | $1.5 \times 10^{-5}$ |
| Tyrosine | $1.5 \times 10^{-5}$ |
| Valine | $3.0 \times 10^{-4}$ |
| Group (b): | |
| Alanine | $1.0 \times 10^{-4}$ |
| Asparagine | $1.0 \times 10^{-4}$ |
| Aspartate | $3.0 \times 10^{-4}$ |
| Glutamate | $1.0 \times 10^{-4}$ |
| Glycine | $1.0 \times 10^{-4}$ |
| Proline | $3.0 \times 10^{-4}$ |
| Serine | $6.0 \times 10^{-4}$ |
| Group (c): | |
| Biotin | $6.0 \times 10^{-8}$ |
| Folate | $1.8 \times 10^{-6}$ |
| Lipoate | $1.0 \times 10^{-6}$ |
| Niacinamide | $3.0 \times 10^{-7}$ |
| Pantothenate | $1.0 \times 10^{-6}$ |
| Pyridoxine | $3.0 \times 10^{-7}$ |
| Riboflavin | $1.0 \times 10^{-7}$ |
| Thiamin | $1.0 \times 10^{-6}$ |
| Vitamin B12 | $3.0 \times 10^{-7}$ |
| Group (d): | |
| Adenine | $1.8 \times 10^{-4}$ |
| Thymidine | $3.0 \times 10^{-6}$ |
| Group (e): | |
| Acetate | $3.7 \times 10^{-3}$ |
| Choline | $1.0 \times 10^{-4}$ |
| Glucose | $6.0 \times 10^{-3}$ |
| i-Inositol | $1.0 \times 10^{-4}$ |
| Putrescine | $1.0 \times 10^{-6}$ |
| Pyruvate | $5.0 \times 10^{-4}$ |
| Group (f): | |
| Magnesium | $6.0 \times 10^{-4}$ |
| Postassium | $1.5 \times 10^{-3}$ |
| Sodium | $1.5 \times 10^{-1}$ |
| Chloride | $1.3 \times 10^{-1}$ |
| Phosphate | $2.0 \times 10^{-3}$ |
| Sulfate | $4.5 \times 10^{-6}$ |
| Group (g): | |
| Copper | $1.0 \times 10^{-8}$ |
| Iron | $1.5 \times 10^{-6}$ |
| Zinc | $3.0 \times 10^{-6}$ |
| Group (h): | |
| Bicarbonate | $1.4 \times 10^{-2}$ |
| HEPES | $2.8 \times 10^{-2}$ |
| Group (i): | |
| Ethanolamine | 0.1 mmol. |
| Phosphoethanolamine | 0.1 mmol. |
| Calcium | 0.1 mmol. |

Weights of each of the above components in the medium may be varied within the concentrations described herein to provide formulations workable within the description of the present invention.

Preferably, the component to be incorporated into the modified MCDB 153 composition, according to the present invention, includes human growth hormone in an amount of at least 0.05 ng/ml.

In addition to effective amounts of cellular growth stimulating hormone and serum free cellular nutrient media, formulations according to the present invention may also contain hydrocortisone and insulin/transferrin, which in certain instances have a beneficial overall effect in enhancing wound healing.

Hydrocortisone was found to improve the cloning efficiency of fibroblasts, enhancing the maintenance of epidermal keratinocytes. The preferred amount to be incorporated is generally in the range of about 0.2 umol. to about 50 umol.

Insulin/transferrin is also an optional desirable constituent, found to impart a maturing stimulus of the growing culture. The preferred amount is in the range of about 0.1 ug to about 50 ug/ml.

The formulations according to the present invention may also include an effective amount of an antimicrobial agent, for example, antibiotics, antifungal agents, such as griseofulvin and nystatin and antiviral agents and the like. The antimicrobial agent may be added for its ability to treat an infection, or alternatively, for its prophylactic effect in avoiding an infection. Where antimicrobial agents are contemplated for use in the present invention, an amount effective to treat an infection or a prophylactic amount of such agent is chosen. The amount of antimicrobial agent used is that amount typically used in topical applications. One of ordinary skill in the art can easily determine the type and amount of antimicrobial agent chosen for use in formulations according to the present invention. In general, the amount of antimicrobial agent may vary widely according to the efficacy of the agent to be delivered and the prophylactic treatment or the severity of the infection. However, in general, the amount of antimicrobial agent to be used in the present invention will range from about 0.05 ug/ml to about 250 mg/ml with a preferred range of about 50 to about 200 ug/ml. Of course, these ranges will vary depending upon the condition of the infection to be treated as well as the strength of the antimicrobial agent employed. For example, in the case of treatment of fungal infections, the amount of amphotericin used generally ranges from about 0.1 ug/ml to about 100 ug/ml with a preferred concentration of about 0.25 ug/ml. In the case of antibiotics and in particular, penicillin, streptomycin and gentamycin, these agents are generally utilized within the concentration range of about 0.05 ug/ml to about 250 mg/ml. with a preferred concentration range of about 25 ug/ml to about 250 ug/ml.

In the case of the use of antibiotics, any number of antibiotics may be used, including aminoglycosides, sulfa drugs, penicillins and chloramphenicol, among others, but it is preferable to use the broad spectrum antibiotics, for example, a cephalosporin or tetracycline in a prophylactic amount or alternatively, in an amount effective for treating a bacterial infection. In using antibiotics, one of ordinary skill in the art will recognize to minimize or avoid the use of antibiotics which may produce allergic reactions in the treated patients.

In certain embodiments according to the present invention, the formulations as described herein are further formulated with hydrogels or related delivery polymers for delivering the formulations according to the present invention to the wound. In these embodiments, the formulations comprising effective amounts of cellular growth stimulating hormone and serum free cellular nutrient media, either alone or in addition to additional components, are admixed with a delivery polymer, for example a hydrogel such as HEMA (hydroxyethylmethacryalte) or NVP (N-vinylpyrrolidone), polyethylene glycol (PEG), gelatin or collagen to promote wound healing. In addition to accelerating wound healing through application of the formulations of the present invention, the compostions which are formulated with a delivery polymer also exhibit the added benefit of preventing or slowing the formation of a scab on the wound. While not being limited by way of theory, it is believed that the resultant wound tissue, which remains soft and moist instead of dry and scab-like, produces a beneficial and increased rate wound-healing.

In a method for treating wounds according to the present invention, the formulations as described hereinabove are topically applied to the wound tissue as a liquid or gel at least once a day and up to six times a day. In the case of formulations containing a delivery polymer, the formulations may be administered less frequently than when the formulations are applied as a liquid. One of ordinary skill in the art will readily determine the amount and frequency of administering the formulations according to the present invention.

Preliminary bioassays to determine the acceleration of wound healing which were carried out on rats, guinea pigs and on selected clinical cases indicated that the formulations according to the present invention exhibited a significant beneficial result relative to traditional therapies.

The invention will be hereinafter described by a number of Examples which illustrate some actual tests carried out on wounds treated with the compositions according to the present invention. It should be understood that the Examples are not exhaustive and are presented only for a better understanding of the invention.

EXAMPLE 1

Wound-Healing Formulation 100 g. of Lyophilized powder of MCDB 153 was reconstituted with distilled, sterilized $H_2O$ and supplemented with human growth hormone to a final concentration of about 0.5 to about 2 ng/ml by conventional mixing. In certain formulations, an amount of insulin-transferrin was added to a final concentration of about 5 µg/ml. The resulting solution was used to treat wounds as exemplified by the following wound-treatment examples. In certain instances, 4% by weight gelatin or collagen is added to provide a gel product for delivery to wounds as indicated.

EXAMPLE 2

Heel Decubitus-pressure wound.

A woman suffering from an acute Toxic Epidemolysis Necrosis (TEN), due to hypersensitivity to sulfa medication (see photo 1(a)) developed an oval shape pressure wound (10×5×2) on her right heel. Conservative treatment failed to produce a successful result.

First treatment consisted of the application of a liquid composition of the formulation according to the present invention containing 1.0 ng/ml of human growth hormone and covered by a bandage.

Three days later, the bandage, stained with exudate which seeped through, was removed. Proliferation of granulation tissue was noticed in the wound bed. The initial oval-shaped contour of the boundary was now keyhole-shaped, having a size of 7×3×1 cm [see photo 1(b)]. A similar treatment with the same composition as above was applied on the wound.

Three days later, the bandage was found to be dried and was removed. The wound appeared to be substantially narrowed and had a size of 5×1.5×0.5 cm [see photo 1(c)]. The granulation tissue in the wound was highly vascularized. A similar treatment with the same composition as above was applied. Three days later the dry bandage was removed and the wound was found to be completely closed.

EXAMPLE 3

Old chronic leg wound.

A 16 month old chronic tapered-oval-shaped crural ulcer (7×3.5×2 cm) was located on the anterior aspect of the upper third tibia. A conventional treatment which was applied was repeatedly unsuccessful.

A collagen gel of the composition according to Example 1 containing 0.5 ng/ml of growth human hormone was applied and covered by a bandage.

Three days later, the exudate-stained bandage was removed. Granulation tissue and vascularization were clearly noticed in the wound bed. The size of the wound was found to be 5.5×2.5×1 cm and its contours was rounded-oval-shaped. A second treatment with the same collagen gel of the modified MCDB 153 composition as above was applied.

Four days later, the bandage was removed; the wound bed revealed highly vascularized granulation tissue. The wound has a spindle-shape and its size was 4×2×0.5 cm. Three days later, the bandage was removed. The wound had an oval shape with a size of 3×1.0×0.25 cm. The same collagen gel treatment as above was applied. Four days later, the bandage was removed and the size of the wound was found to be 2.5×1×0 cm.

After a few days the patient informed that the wound was completely closed.

Figure 2:
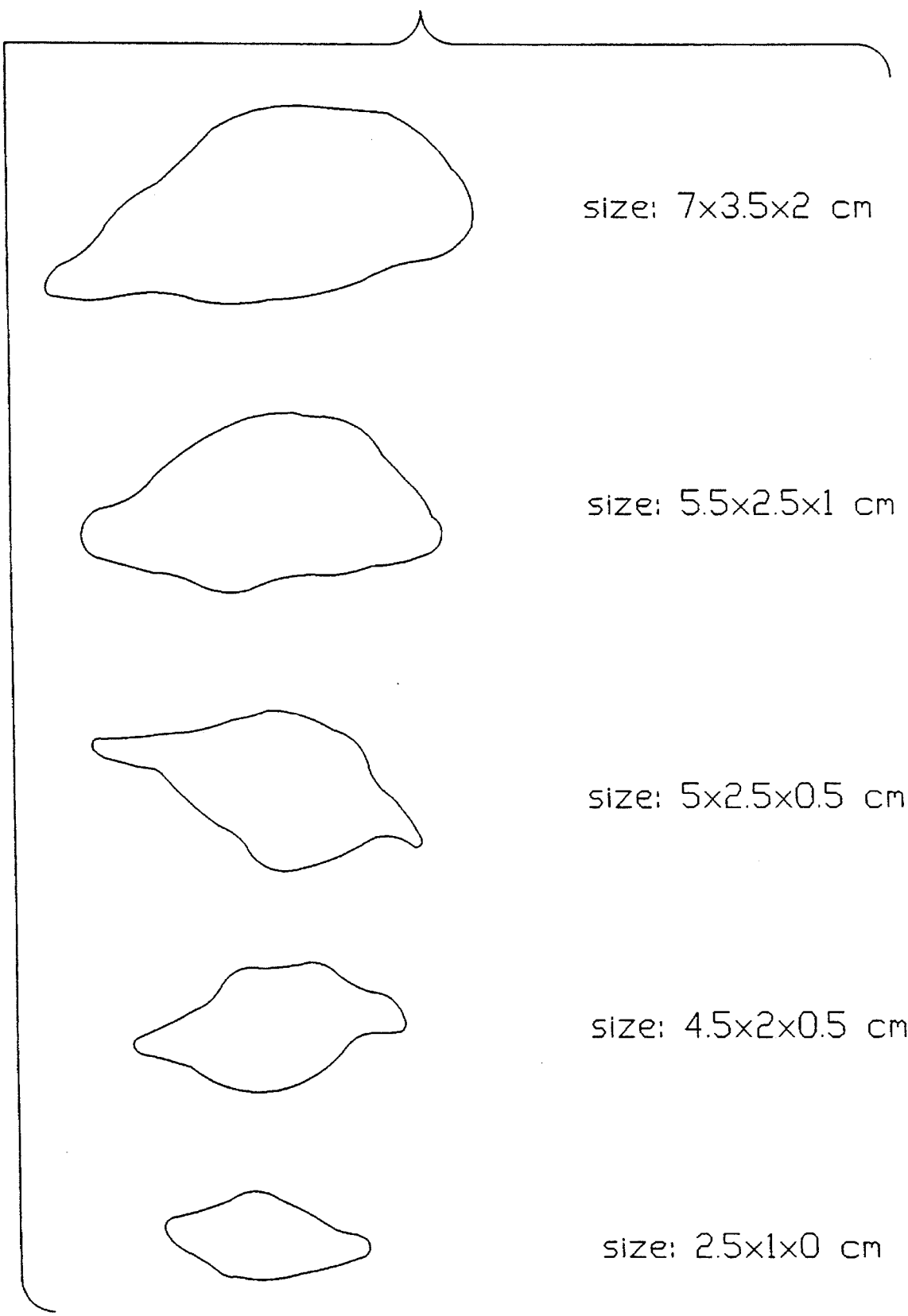

A graphic illustration on the shapes of the wound at certain intervals is presented in FIG. 2.

EXAMPLE 4

A wound caused by a bilateral recurrent crural ulcer. The ulcer wound (10×7.1×1.5 cm) did not respond to any conventional treatment.

In the first treatment a solution of Example 1 containing 2 ng/ml of human growth hormone and 5 ug/ml of Insulin was applied.

A week later, the fibril exudate-stained bandage was removed. A considerable granulation tissue proliferation was noticed that raised the bed of the wound. The size of the wound was found to be 8×5×0.5 cm. The wound was washed with a solution (3% by vol.) of hydrogen peroxide and the same solution as in the first treatment was applied.

Four days later, the bandage was removed and it was noticed that granulation tissue filled most of the gap of the wound which was clean.

A split-skin graft surgery was further applied.

I claim:

1. A wound healing formulation comprising a wound healing effective amount of human growth hormone in combination with an amount of insulin in a concentration ranging from about 0.1 ug/ml to about 50 ug/ml in a serum free cellular nutrient medium, said nutrient medium comprising wound healing effective amounts of essential amino acids, non-essential amino acids, glucose, a mixture of vitamins comprising folate, niacinamide, pantothenate, pyridoxine, riboflavin and thiamin and a mixture of inorganic ions comprising calcium, sodium, potassium, magnesium and chloride.

2. The formulation according to claim 1, wherein the human growth hormone is included within a concentration range of about 0.5 ng./ml. to about 50 ng./ml.

3. The formulation according to claim 1 wherein said formulation is a liquid.

4. The formulation according to claim 1 further comprising an amount of water and a delivery polymer effective to gel said formulation.

5. The formulation according to claim 4 wherein said delivery polymer is selected from the group consisting of hydroxyethylmethacrylate, polyvinylpyrrolidone, polyethylene glycol, gelatin and collagen.

6. The formulation according to claim 4 wherein said formulation is a gel.

7. The formulation according to claim 1 wherein said serum free nutrient media is selected from the group consisting of ADC-1, LPM (Albumin-free), F10, F12, DCCM1, DCCM2, BGJ Medium (Fitton-Jackson Modification), Basal Medium Eagle (BME-with the addition of Earle's salt base), Dulbecco's Modified Eagle Medium (without serum), Glasgow Modification Eagle Medium (GMEM), Leibovitz L-15 Medium, McCoy's 5A Medium, MDCB 153, Medium M199 (M199E- with Earle's salt base), Medium M199 (M199H- with Hank's salt base), Minimum Essential Medium Eagle (MEM-E- with Earle's salt base), Minimum Essential Medium Eagle (MEM-H- with Hank's salt base) and Minimum Essential medium Eagle (with non-essential amino acids).

8. The formulation according to claim 1 wherein said nutrient medium is MDCB 153.

9. The formulation according to claim 1 further including an effective amount of an antimicrobial agent.

10. The method according to claim 9 wherein said formulation is a gel.

11. A method for enhancing the rate of wound healing in animals comprising applying to a wound a formulation comprising a wound healing effective amount of human growth hormone in combination with an amount of insulin in a concentration ranging from about 0.1 ug/ml to about 50 ug/ml in a serum free cellular nutrient medium, said nutrient medium comprising wound healing effective amounts of essential amino acids, non-essential amino acids, glucose, a mixture of vitamins comprising folate, niacinamide, pantothenate, pyridoxine, riboflavin and thiamin and a mixture of inorganic ions comprising calcium, sodium, potassium, magnesium and chloride.

12. The method according to claim 11 wherein the human growth hormone is included within a concentration range of about 0.5 ng./ml. to about 50 ng./ml.

13. The method according to claim 11 wherein said formulation is a liquid.

14. The method according to claim 11 further comprising an amount of water and a delivery polymer effective to gel said formulation.

15. The method according to claim 14 wherein said delivery polymer is selected from the group consisting of hydroxyethylmethacrylate, polyvinylpyrrolidone, polyethylene glycol, gelatin and collagen.

16. The method according to claim 11 wherein said serum free nutrient media is selected from the group consisting of ADC-1, LPM (Albumin-free), F10, F12, DCCM1, DCCM2, BGJ Medium (Fitton-Jackson Modification), Basal Medium Eagle (BME-with the addition of Earle's salt base), Dulbecco's Modified Eagle Medium (without serum), Glasgow Modification Eagle Medium (GMEM), Leibovitz L-15 Medium, McCoy's 5A Medium, MDCB 153, Medium M199 (M199E- with Earle's salt base), Medium M199 (M199H- with Hank's salt base), Minimum Essential Medium Eagle (MEM-E- with Earle's salt base), Minimum Essential Medium Eagle (MEM-H- with Hank's salt base)

and Minimum Essential Medium Eagle (with non-essential amino acids).

17. The method according to claim 16 wherein said nutrient media is MDCB 153.

18. The method according to claim 11 wherein said formulation further includes an effective amount of an antimicrobial agent.

19. A method for treating wounds in an animal, comprising applying to said wound a formulation comprising an amount of human growth hormone in combination with an amount of insulin ranging from about 0.1 ug/ml to about 50 ug/ml in MCDB 153, said growth hormone and said insulin being included in said formulation in wound healing effective amounts.

20. A wound healing formulation comprising a wound healing effective amount of human growth hormone in combination with a wound healing effective amount of insulin at a concentration ranging from about 0.1 ug/ml to about 50 ug/ml in MCDB 153.

21. The formulation according to claim 20 further comprising tri-iodothyronine in an amount ranging from about 0.5 ng/ml to about 50 ng/ml.

22. A method for treating wounds in an animal comprising applying to said wound a formulation comprising a wound healing effective amount of human growth hormone in combination with a wound healing effective amount of insulin at a concentration ranging from about 0.1 ug/ml to about 50 ug/ml in MCDB 153.

* * * * *

UNITED STATES PATENT AND TRADEMARK OFFICE
CERTIFICATE OF CORRECTION

PATENT NO. : 5,461,030
DATED : Oct. 24, 1995
INVENTOR(S) : Ella Lindenbaum

It is certified that error appears in the above-indentified patent and that said Letters Patent is hereby corrected as shown below:

Cover Page, under "Foreign Application Priority Data", delete "Feb. 1, 1991    [IL]    Israel ............... 097127"

Column 1, line 4, insert -- CROSS-REFERENCE TO RELATED APPLICATIONS

This application is a continuation of commonly owned application Ser. No. 07/752,849 filed Aug. 30, 1991, now abandoned. --

Column 3, line 2, delete "between".

Column 4, line 15, change "human growth human" to --human growth hormone--; line 19, delete "(EGF)"; line 45, insert --,-- after "well-known"; line 67, change "(k)" to --(i)--.

Column 5, line 4, delete "the mechanism of the accelerated wound healing, but a plausible explanation could be that".

Column 8, line 3, change "compostions" to --compositions--.

Column 10, line 24, change "medium" to --Medium--.

Signed and Sealed this

Seventh Day of May, 1996

Attest:

BRUCE LEHMAN

Attesting Officer

Commissioner of Patents and Trademarks